United States Patent
Suh et al.

[11] Patent Number: 6,031,061
[45] Date of Patent: Feb. 29, 2000

[54] BIS (TRIAKLYLTRIMELLITIC ANHYDRIDE) DERIVATIVE AND POLYESTERIMIDE FOR OPTICAL COMMUNICATIONS FORMED THEREFROM

[75] Inventors: Dong-hack Suh, Daejeon; Sun-young Chung, Chungcheongnam-do; Tae-hyung Rhee, Sungnam, all of Rep. of Korea

[73] Assignee: SamSung Electronics Co., Ltd., Kyungki-do, Rep. of Korea

[21] Appl. No.: 09/223,568

[22] Filed: Dec. 31, 1998

[30] Foreign Application Priority Data

Dec. 31, 1997 [KR] Rep. of Korea ............... 97-82005

[51] Int. Cl.[7] .................. C08G 73/16; C07C 51/00; C07C 63/00; C07D 307/77
[52] U.S. Cl. .................. 528/170; 528/125; 528/128; 528/170; 528/174; 528/179; 528/183; 528/185; 528/188; 528/272; 528/288; 528/310; 528/322; 528/350; 528/353; 528/274; 549/241; 549/245; 549/246
[58] Field of Search .................. 549/241, 245, 549/246; 528/170, 310, 322, 274, 288, 272, 125, 128, 174, 179, 183, 185, 188, 350, 353

[56] References Cited

U.S. PATENT DOCUMENTS

| | | | |
|---|---|---|---|
| 3,876,668 | 4/1975 | Knobloch | 549/245 |
| 4,001,179 | 1/1977 | Richter et al. | 548/462 |
| 4,785,121 | 11/1988 | Leone-Bay et al. | 549/246 |
| 4,940,802 | 7/1990 | Matsuba et al. | 548/462 |
| 5,086,188 | 2/1992 | Fertel et al. | 549/246 |
| 5,102,981 | 4/1992 | Kan | 528/322 |
| 5,233,049 | 8/1993 | Dinan et al. | 548/462 |
| 5,391,697 | 2/1995 | Furutani | 528/288 |
| 5,693,797 | 12/1997 | Day | 544/198 |

OTHER PUBLICATIONS

Chem. Abs. 66:29545 & FR 1422945 (Thomson–Houston) Loncrini, Donald F. Jan. 1966.

Abstract of JP 3058982 A (Hitachi Chem) Yusa Masami, ea al. Mar. 1991.

Chem. Abs. 78:160777 & Vysokomol. Soedin., A (1973), 15(2), 310–13 M.M.Koton, "Synthesis, Structure, and Properties of Polyester Imides".

*Primary Examiner*—P. Hampton-Hightower
*Attorney, Agent, or Firm*—Robert E. Bushnell, Esq.

[57] ABSTRACT

A bis(trisubstitutedtrimellitic anhydride) derivative and a polyesterimide for optical communications, the polyesterimide being formed therefrom. The polyesterimide has a high refractive index, so that when using such polyesterimide as a material for a core of an optical fiber, the range of materials that can be selected for the cladding becomes wide. Also, a coating property and adhesion to a substrate are improved, thereby providing a good film forming property and thermal stability. Also, because the polyesterimide can minimize optical loss at a near infrared wavelength range, the polyesterimide is very useful as an optical material in the optical communications field adopting the light of near infrared wavelength.

16 Claims, No Drawings

BIS (TRIAKLYLTRIMELLITIC ANHYDRIDE) DERIVATIVE AND POLYESTERIMIDE FOR OPTICAL COMMUNICATIONS FORMED THEREFROM

This application makes reference to, incorporates the same herein, and claims all benefits accruing under 35 U.S.C. §119 from an application for BIS (TRIALKYLTRIMELLITIC AHYDRIDE) DERIVATIVE AND POLYESTERIMIDE FOR OPTICAL COMMUNICATIONS FORMED THEREFROM earlier filed in the Korean Industrial Property Office on Dec. $31^{st}$ 1997 and there duly assigned Ser. No. 97-82005.

BACKGROUND OF THE INVENTION

1. Field of the Invention

The present invention relates to materials for optical communications, and more particularly, to a polyesterimide for optical communications, which minimizes optical loss in a near infrared wavelength range.

2. Description of the Related Art

A wavelength range for optical communications has been shifted from 800 nm to 1550 nm, which corresponds to the near infrared wavelength range. Thus, it is ideal to manufacture an optical communication device using a material which barely absorbs light belonging to the wavelengths of the near infrared range.

A polymer is generally used for an optical substrate such as an optical lens or compact disk. Recently, many attempts have been made to use such polymers as optical waveguide materials for light transfer in the near infrared wavelength range.

A conventional polymer generally absorbs light of 1000–1700 nm which corresponds to the near infrared wavelength range. Such absorption of light in the near infrared wvavelength range by the polymer is caused by overtone of harmonics due to stretching and deformation vibrations of carbon-hydrogen (C—H) bonds in alkyl phenyl and other similar finctional groups. Thus, it is not desirable to use such a conventional polymer as the optical waveguide material utilizng the light of the near infrared wavelength range because of a large optical loss. In order to reduce the optical loss, the light absorption wavelength region of a polymer must be shifted from the near infrared wavelength range to a longer or shorter wavelength region. To this end, a method in which hydrogen in the C—H bond is substituted by fluorine (F) or deuterium (D) has been suggested.

Particularly, in the case of substituting hydrogen with deuterium, a C—D bond causes light absorption at the wavelength range of about 1500 nm. Deuterium-substituted polymers are therefore not suitable for materials for optical communications devices using the 1500 nm wavelength range. On the other hand, substitution of hydrogen by fluorine can minimize optical loss in light absorption at a wavelength in the range of 1000–1700 nm.

An optical material used for fabricating optical devices such as an opto-electronic integrated circuit (OEIC), an opto-electrical mixed wiring board (OEMWB), a hybrid integration device, a plastic optical fiber or a multi-chip module (CM) must have good thermal stability during a fabrication process, particularly at a temperature of about 250° C. Since the thermal stability of an optical material is a very important factor, careful consideration must be taken of the glass transition temperature, thermal decomposition temperature, thermal expansion coefficient or birefingence of the optical material.

Polyimide has been most widely known as a polymer having good thermal stability. Since polyimide is stable at a high temperature of about 400° C., great efforts to utilize polyimide as a material for optical communications have been consistently made.

However, generally, since a conventional polyimide has many C—H bonds in its molecule structure, it exhibits a large optical loss in the near infrared region To overcome this problem, recently, a method in which hydrogen in C—H bonds of a polyimide is partially or entirely substituted by fluorine has been proposed.

However, if hydrogen is substituted by fluorine, the refractive index of the polymer is decreased. Here, the content of fluorine in the polymer is proportional to the decreased level of the refractive index. Thus, since a polyimide obtained by substituting hydrogen in the C—H bonds by is fluorine, that is, a fluorinated polyimide, has a low refractive index, in the case of using the fluorinated polymer as a core, the range of selection of materials capable of being used for cladding becomes narrow.

Also, the higher the content of fluorine in the polyimide is, the lower the surface tension of a composition containing the polyimide is. Thus, it is difficult to coat such a composition on a substrate and the adhesion of a film comprised of the composition is poor. As a result, film characteristics are deteriorated and the film formed thereby is very fragile. Thus, it is very difficult to put the polylmide into practical use for an optical communications material.

SUMMARY OF THE INVENTION

It is therefore an object of the present invention to provide an improved optical polymer for use in optical communications.

It is a further object of the present invention to provide a polymer for optical communications which minimizes optical loss in the near infrared wavelength of 1,000 to 1,700 nm It is a yet further object to provide a polymer for optical communications which has good thermal stability at 200° C. or more.

It is a still further object to provide a polymer for optical communications which has good film processing properties.

To achieve the above objects, the present invention provides a polyesterimide for optical communications. According to an aspect of the present invention, there is provided a bis(trisubstitutedtrimellitic anhydride) derivative represented by the chemical formula (1):

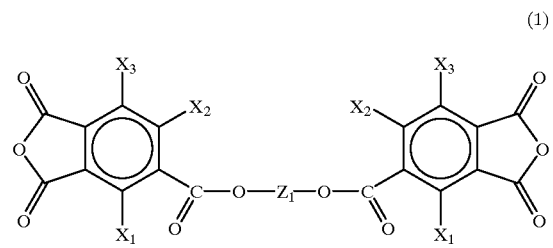

wherein $X_1$, $X_2$ and $X_3$ are independenty selected from the group consisting of halogen atom, halogenated alkyl group, halogenated aromatic ring group, —$NO_2$, —$OR^1$ and $SR^1$ (where $R^1$ is halogenated alkyl or halogenated aromatic ring group); and $Z_1$ is selected from the group consisting of divalent halogenated aliphatic hydrocarbon, divalent halogenated aliphatic cyclic hydrocarbon and divalent halogenated aromatic hydrocarbon.

According to another aspect of the present invention, there is provided a polyesterimde for optical communications, comprising a repeating unit represented by the chemical formula (2):

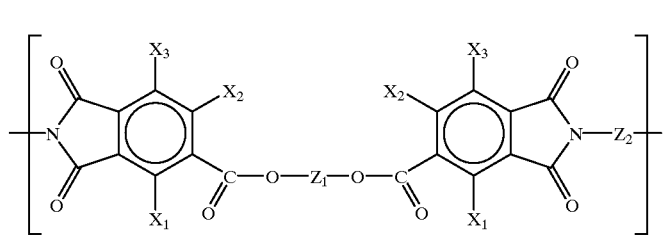

(2)

wherein $X_1$, $X_2$ and $X_3$ are independently selected from the group consisting of halogen atom, halogenated alkyl group, halogenated aromatic ring group, —$NO_2$, —$OR^1$ and $SR^1$ (where $R^1$ is halogenated allyl or halogenated aromatic ring group); and $Z_1$ and $Z_2$ are independently selected from the group consisting of divalent halogenated aliphatic hydrocarbon, divalent halogenated aliphatic cyclic hydrocarbon and divalent halogenated aromatic hydrocarbon.

Preferably, $X_1$, $X_2$ and $X_3$ are independently selected from the group consisting of chlorine atom, partially or perchlorinated alkyl groups, partially or perchlorinated aromatic ring groups, partially or perchlorinated alkoxy groups, and partially or perchlorinated phenoxy groups.

Preferably, $Z_1$ and $Z_2$ are independently selected from the group consisting of divalent halogenated aliphatic hydrocarbon of $C_1$–$C_{25}$, divalent halogenated aliphatic cyclic hydrocarbon of $C_1$–$C_{25}$ and divalent halogenated aromatic hydrocarbon of $C_6$–$C_{25}$. More preferably, $Z_1$ and $Z_2$ are independently selected from the group represented by the following structural formulae:

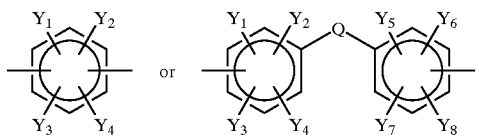

wherein $Y_1$, $Y_2$, $Y_3$, $Y_4$, $Y_5$, $Y_6$, $Y_7$ and $Y_8$ and are independently selected from the group consisting of halogen atom, halogenated alkyl group, halogenated aromatic ring group, —$NO_2$, —$OR^1$ and $SR^1$ (where $R^1$ is halogenated alkyl or halogenated aromatic ring group); and Q is either a single chemical bond or is selected from the group consisting of, —O—, —CO—, —$SO_2$—, —S—, —$(OT)_m$—, $(TO)_m$— and —$(OTO)_m$— and (where T is halogenated alkylene or halogenated arylene group and m is an integer from 1 to 10). Here, the structural formulae indicate that the substitution position of the Y-groups is not specified.

Preferably, the polyesterimide has a molecular weight in the range of approximately $1 \times 10^4$ to $5 \times 10^5$ Dalton, and has a thermal decomposition temperature in the range of approximately 300 to 500° C., thereby having good thermal stability.

DESCRIPTION OF THE PREFERRED EMBODIMENTS

A bis(trisubstitutedtrimellitic anhydride) derivative according to the present invention is usable as an intermediate for synthesizing a polyesterimide for optical communications. In the polyesterimide for optical communications according to the present invention, hydrogen of a C—H bond is substituted with a halogen atom or a nitro group. Here, the halogen atom substituted for the hydrogen is not limited to a specific halogen element, and combinations of various halogen atoms are possible. Preferably, the hydrogen of C—H bond of the polyesterimide is substituted with chloride (Cl). This is because the optical loss caused by a C—Cl bond is less than that by the C—H bond.

Hereinafter, a method for synthesizing the bis (trisubstitutedtrimellitic anhydride) derivative according to the present invention will be described. First, referring to the reaction formula (3), a halogenated compound or a nitrating agent is reacted with 1,2,4-trimethylbenzene (D) to synthesize 3,5,6-trisubstituted-1,2,4-trimethylbenzene (E). The 3,5,6-trisubstituted-1,2,4-trimethylbenzene (E) is oxidized by various oxidation methods utilizing, e.g., transition metal catalyst, potassium permanganate or nitric acid, resulting in 3,5,6-trisubstitutedbenzene-1,2,4-tricarboxylic acid (F).

Referring to the reaction formula (4), acetic acid and an acetic anhydride are added to the 3,5,6-trisubstitutedbenzene-1,2,4-tricarboxylic acid (F), and then the mixture is reacted, resulting in a mononer, 3,5,6-trisubstituted-4-carboxylic acid-1,2-phthalic anhydride (G).

The 3,5,6-trisubstituted-4-carboxylic acid-1,2-phthalic anhydride (G) is reacted with a halogenated compound such as thionyl chloride, to synthesize 3,5,6-trisubstituted-4-halogenformylphthalic anhydride (A).

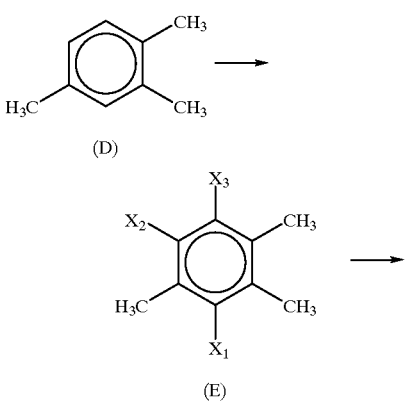

(3)

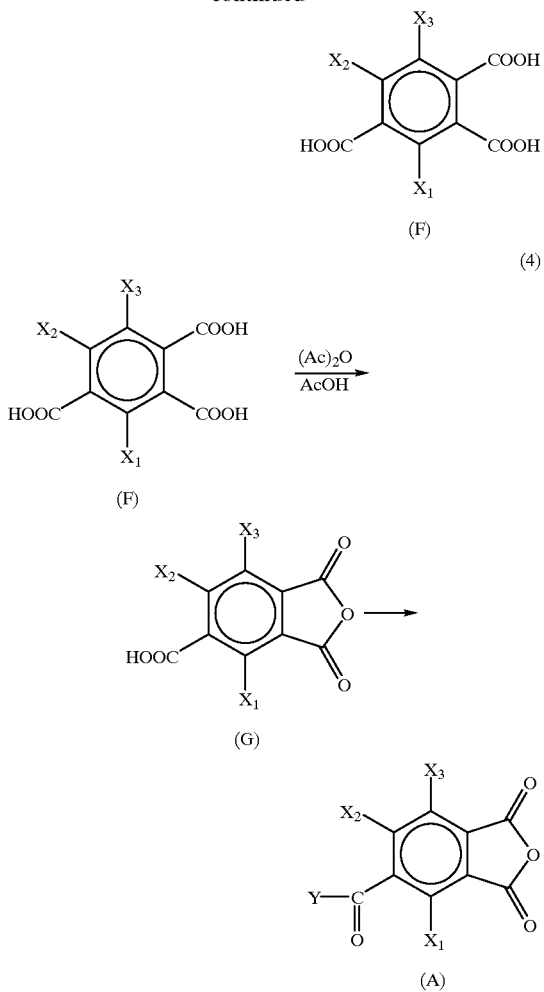

In the reaction formulae (3) and (4), $X_1$, $X_2$, and $X_3$ are independently selected from the group consisting of halogen atom, halogenated allyl group, halogenated aromatic ring group, —$NO_2$, —$OR^1$ and $SR^1$ (where $R^1$ is halogenated alkyl or halogenated aromatic ring group).

The 3,5,6-trisubstituted-4-halogenformylphthalic anhydride (A) is reacted with a diol compound (HO—$Z_1$—OH wherein $Z_1$ is divalent halogenated aliphatic hydrocarbon, divalent halogenated aliphatic cyclic hydrocarbon or divalent halogenated aromatic hydrocarbon), resulting in a bis(trisubstitutedtrimellitic anhydride) derivative represented by the chemical formula (1).

(1)

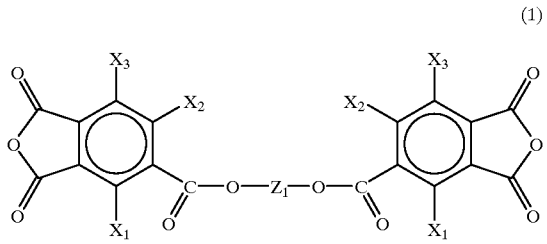

In the chemical formula (1), $X_1$, $X_2$, and $X_3$ are independently selected from the group consisting of halogen atom, halogenated alkyl group, halogenated aromatic ring group, —$NO_2$, —$OR^1$ and $SR^1$ (where $R^1$ is halogenated alkyl or halogenated aromatic ring group); and $Z_1$ is selected from the group consisting of divalent halogenated aliphatic hydrocarbon, divalent halogenated aliphatic cyclic hydrocarbon and divalent halogenated aromatic hydrocarbon.

The synthesis of the bis(trisubstitutedtrimellitic anhydride) derivative represented by the chemical formula (1) under specific reaction conditions will be described in detail.

1,2,4-Trimethylbenzene and iodine are added to chloroform, and hydrogen bromide, hydrogen chloride, hydrogen fluoride or nitric acid is added to the mixture, and then vigorously stirred at 0~40° C. for 15 minutes to 24 hours. After the reaction is completed, the resulting precipitate is filtered.

Pyridine and water are added to the resulting product, and then heated at 100° C. Then, potassium permanganate is added to the reaction mixture and then reacted at 50~115° for 2~24 hours. Then, the resulting product is immediately filtered without cooling. The obtained resultant is distilled in a vacuum, and pyridine is removed from the resultant product. Water and sodium hydroxide are added to the remaining residue and then heated at 50~100°.

After potassium permanganate is added to the resulting mixture and then reacted for 2~24 hours, the reaction mixture is acidified using 5N HCl aqueous solution. Then, the solvent is removed from the reaction mixture, resulting in 3,5,6-trisubstitutedbenzent-1,2,4-tricarboxylic acid.

Acetic acid and acetic anhydride are added to the 3,5,6-trisubstitutedbenzene-1,2,4-tricarboxylic acid, and then reacted at 50~130° C. for 30 minutes to 24 hours, resulting in 3,5,6-trisubstituted-4-carboxylic acid-1,2-phthalic anhydride. The 3,5,6-trisubstituted-4-carboxylic acid-1,2-phthaiic anhydride is reacted with thionyl chloride at 30° C. for 30 minutes to 48 hours, resulting in a 3,5,6-trisubstituted-4-halogenformylphthalic anhydride.

The 3,5,6-trisubstituted-4-halogenformylphthalic anhydride is mixed with a diol compound, pyridine and acetonitrile, and then reacted at −40~10° C. for 1~24 hours. After the reaction is completed, the resulting precipitate is removed from the reaction mixture, washed with chloroform and then dried, resulting in the bis(trisubstitutedtrimelltic anhydride) derivative represented by the chemical formula (1).

The diol compound is not limited to a specific compound. For example, possible diol compounds include bis(perfluorophenyl)alkanes, bis(perfluorophenyl)sulfones, bis(perfluorophenyl)ethers or α,α'-bis(perfluorophenyl)diisopropylbenzenes. In detail the diol compound may be hexafluoro-1,5-pentanediol, 2,2,3,3,4,4,5,5-octafluorohexane-1,6-diol, 2,2,3,3-tetrafluorobutane-1,4-diol, 2,2,3,3,4,4,5,5,6,6,7,7-dodecafluoro-1,1-heptanediol, 2,2,3,3,3,4,4,5,5,6,6,7,7-dodecafluoro-1,8-octane-diol, 3,3,4,4,5,5,6,6-octafluorooctane- 1,8-diol, 2,2,3,3,4,4,5,5,6,6,7,7,8,8-tetradecafluorononane, 1H,1H,2H,3H,3H-perfuorononane-1,2-diol, 7H-dodecafiuoro-1,1-heptanediol, 1H,1H,10H,10H-hexadecafiuorodecane-1,10-diol, 1H,1H,10H,10H-perfluorodecane-1,10-diol, 1H,1H,2H,3H,3H-perfluoroundecane-1,2-diol, tetafluoronone-1,9-diol, tetrafluorohydroquinone, tetrachlorohydroquinone, 2,2-bis(3-amino-4-hydroxyphenyl) hexafluoropropane, 2,2-bis(3-amino-4-hydroxyphenyl)hexachloropropane, 2,2-bis[4-(2-hydroxyethoxy)phenyl]hexafluoropropane, 2,2-bis[4-(2-hydroxyethoxy)phenyl]hexachloropropane, 1,3-bis(2-hydroxyhexafluoroisopropyl)benzene, 1,4-bis(2-hydroxyhexafluoroisopropyl)benzene, 4,4'-bis (2-hydroxyhexafluoroisopropyl) diphenyl, 4,4'-bis(2-hydroxyhexafluoroisopropyl)diphenylether, 2,2-bis(4-hydroxyphenyl)hexafluoropropane, 1,3-bis(2-hydroxyhexachloroisopropyl)benzene, 1,4-bis(2-hydroxyhexachloroisoporpyl)benzene, 4,4'-bis(2-hydroxyhexachloroisopropyl)diphenyl 4,4'-bis(2-hydroxyhexachloroisopropyl)diphenylether, 2,2'-bis(4-hydroxyphenyl)hexachloropropane, 1,1-(4,4'-dihydroxydiphenyl)ethane, 1,2-(4,4'-dihydroxydiphenyl)ethane, 1,10-(4,4'-dihydroxydiphenyl)decane, 1,4-(4,4'-dihydroxydiisopropylidenediphenyl)benzene, 1,4-(4,4'-dihydroxydimethylenediphenyl)benzene, 1,10-(4,4'-dihydroxydiphenyl)-1,1-dioxodecane, 4,4'-dihydroxydiphenylether, 4,4'-dihydroxydiphenylsulfide, 4,4'-dihydroxy-3,3'-dimethyldiphenylsulfide, 4,4'-dihydroxydiphenylsulfoxide, 4,4'-dihydroxydiphenylsulfone, 4,4'-dihydroxy-3,3'-dichlorodiphenylsulfone, 4,4'-dihydroxydiphenyl-1,1-butane, 4,4'-dihydroxydiphenyl-1,1-isobutane, 4,4'-dihydroxydiphenyl-1,1-cyclopentane, 4,4'-dihydroxydiphenyl-1,1'-cyclohexane, 4,4'-dihydroxydiphenyl-2,2-butane, 4,4'-dihydroxydiphenyl-2,2-pentane, 4,4'-dihydroxydiphenyl-2,2-(4-methylpentane), 4,4'-dihydroxydiphenyl-4,4-heptane, 4,4'-dihydroxydiphenyl-2,2,2-ethane, 4,4-dihydroxytriphenylmethane, 4,4'-dihydroxy-3,3',5,5'-tetrachlorodiphenyl-1,1-cyclohexane, 4,4'-dihydroxydiphenyl-2,2-hexane, 4,4-dihydroxydiphenyl-β,β-decahydronaphtene, 4,4'-dihydroxydiphenylmethane, 4,4'-dihydroxydiphenyl-2,2-propane, 4,4'-dihydroxy-3,3',5,5'-tetrachlorodiphenyl-2,2-propane, 4,4'-dihydroxy-3,3'-dichlorodiphenyl-2,2-propane, 4,4'-dihydroxy-3,3'-dimethyldiphenyl-2,2-propane, 1,3-propanediol, 1,4-butanediol 1,1'-dihydroxydiethylether, 1,1'-dihydroxydimethyl-2,2-propane, 1,1'-dihydroxydimethyl-2,2-pentane, 1,1'-dihydroxydimethyl-1,4-benzene, 1,1'-dihydroxydiethylbenzene, 1,1'-dihydroxydimethylbenzidie, 1,1'-dihydroxydiethylbenzidine, (1,1'-biphenyl)-2,5-diol, (1,1'-biphenyl)4,4'-diol, (1,1'-biphenyl)-3,4-diol, (1,1'-biphenyl)-3,4'-diol, (1,1'-biphenyl)-2,2'-diol, (1,1'-biphenyl)-3,3'-diol, (1,1'-biphenyl)-2,4'-diol, 3,3'-dimethyl-(1,1'-biphenyl)-4,4'-diol, 5,5'-dimethyl-(1,1'-biphenyl)-2,2'-diol, 3,3'-dimethyl-(1,1'-biphenyl)-2,2'-diol, 6,6'-dinethyl-(1,1'-biphenyl)-2,2'-diol, 5,5'-diethyl-(1,1'-biphenyl)-2,2'-diol, 3,3'-difluoro-(1,1'-biphenyl)-4,4'-diol, 5,5'-difluoro-(1,1'-biphenyl)-2,2'-diol, 3,3'-dimethyl-(1,1'-biphenyl)-2,2'-diol, 3,3'-dimethyl-(1,1'-biphenyl)-4,4'-diol, 6,6'-dimethyl-(1,1'-biphenyl)-2,2'-diol, 6,6'-dimethyl-(1,1'-biphenyl)-3,3'-diol, 5,6'-dimnethyl 6,-dimethyl-(1,1'-biphenyl)-2,3'-diol, 3,3',5,5'-tetrafluoro-(1,1'-biphenyl)-2,2'-diol, 3,3',5,5'-tetramethoxy-(1,1'-biphenyl)-4,4'-diol, 2,2',6,6'-tetramethoxy-(1,1'-biphenyl)-4,4'-diol, 3,3',5,5'-tetramethyl-(1,1'-biphenyl)-4,4'-diol, 3,3',5,5'-tetramethyl-(1,1'-biphenyl)-2,2'-diol, 2,2-bis(4-hydroxyphenyl)-1,3-perfluoropropane, 4,4'-dihydroxybenzophenone, 1,4-bis(4-hydroxyphenyl)benzene, 4,4'-bis(4"-hydroxybenzenesulfonyl)diphenyl, 4,4'-dihydroxy-3,3',5,5'-tetramethyldiphenyl-1,1'-methane, 2,2-bis(4-hydroxy-2,3,5-trichlorophenyl)propane, 4,4'-dihydroxy-3,3',5,5'-tetramethyldiphenyl-1,1-methane, 2,2-bis(4-hydroxy-2,3,5-trichlorophenyl)propane, 4,4'-hydroxy-3,3',5,5'-tetramethyldiphenyl-1,1-cyclohexane, 1,1-bis(4-hydroxy-3-methyl)cyclohexane, 2,4-bis(4-hydroxyphenyl)2-methylbutane, 4,4'-dihydroxy-3,3',5,5'-tatramethyldiphenyl-1,1-sulfone, 2,2-bis(3-hydroxyphenyl)-1,3-perfluoropropane, 4,4'-dihydroxydiphenyl-1,1'-diphenylmethane, 2-bis(4-hydroxyphenyl)-1,1',3,3'-chlorodifluoropropane, 4,4'-dihydroxydiphenyl-1,1'-cyclopentane, 2-methylhydroxyquinone, 4,4'-dihydroxydiphenyl-2,2'-dichloro-1,1'-ethene, or 1,4-bis(4-hydroxyphenyl-2-propyl)benzene.

Hereinafter, a method for synthesizing a polyesterimide for optical communications according to the present invention, from the bis(trisubstitutedtrimellitic anhydride) derivative represented by the chemical formula (1) will be described.

The bis (trisubstitutedtrimellitic anhydride) derivative represented by the chemical formula (1) and a diamine compound ($H_2N-Z_2-NH_2$ wherein $Z_2$ is divalent halogenated aliphatic hydrocarbon, divalent halogenated aliphatic cyclic hydrocarbon or divalent halogenated aromatic hydrocarbon) are dissolved in N,N-dimethylacetamide, dimethylsulfoxide, N-methyl-2-pyrrolidone or N,N-dimethylformamide, and then reacted at −20~50° C. for 2~300 hours. The reaction mixture is precipitated using distilled water or methyl alcohol to yield polyesteramic acid The polyesteirmic acid is imidized, resulting in a polyesterimide represented by the chemical formula (2).

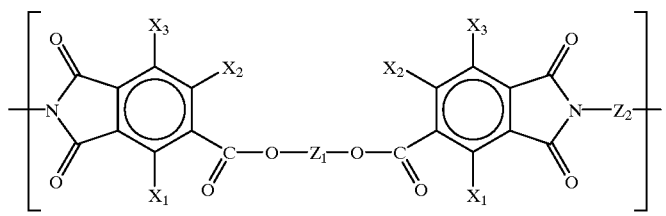

(2)

In the chemical formula (2), $X_1$, $X_2$, and $X_3$, $Z_1$ and $Z_2$ are the same as those described above. Here, the imidation of polyesteramic acid into the polyesterimide is performed by a chemical or thermal method.

In the chemical method, an acetic anhydride and pyridine may be added to the polyesteramic acid and then heated at 130° C. Also, in the thermal method, the polyesteramic acid may be heated at 70° C. for 2 hours, 160° C. for 1 hour or 250° C. for 30 minutes.

The polyesterimide obtained through the above process has a molecular weight in the range of approximately $1\times10^4$ Dalton, preferably, $1.5\times10^4$ to $2.5\times10^4$ Dalton. Here, the molecular weight is measured using gel permeation chromatography.

The thermal decomposition temperature of the polyesterimide, measured by thermogravimetry analysis (TGA), is in the range of approximately 300~500° C., preferably, 375~425° C. Also, the glass transistion temperature of the polyesterimide is 190~290° C.

The diamie compound is not limited to a specific compound. For example, possible diamine compounds include bis(perfluorophenyl)alkanes, bis(perfluorophenyl)sulfones, bis(perfluorophenyl)ethers or α,α'-bisperfluorophenyl) disopropylbenzenes. In detail, the diamine compound (B) may be tetrafluoro-1,2-phenylenediamine, tetrafluoro-1,3-phenylendiamine, tetrafluoro-1,4-phenylenediamine, tetrachloro-1,2-phenylenediamine, tetrachloro-1,3-phenylenediamine, tetrachloro-1,4-phenylenediamine, hexafluoro-1,5-diaminonaphthalene, hexafluoro-2,6-diaminonaphthalene, 3-trifluoromethyltrifluoro-1,2-phenylenediamine, 4-trifluoromethyltrifluoro-1,2-phenylenediamine, 2-trifluoromethylfluoro-1,3-phenylenediamine, 4-trisluoromethyltrifluoro-1,3-phenylenediamine, 5-trifluoromethyltrifluoro-1,3-phenylenediamine, 2-trifluoromethyltrifluoro-1,4-phenylenediamine, 3-pentafluoroethyltrifluoro-1,2-phenylenediamine, 4-pentafluoroethyltrifluoro-1,2-phenylenediamine, 2-pentafluoroethyltrifluoro-1,3-phenylenediamine, 4-pentafluoroethyltrifluoro-1,3-phenylenediamine, 5-pentafluoroethyltrifluoro-1,3-phenylenediamine, 2-pentafluoroethyltrifluoro-1,4-phenylenediamine, 3,4-bis(trifluoromethyl)difluoro-1,2-phenylenediae, 3,5-bis(trifluoromethyl)difluoro-1,2-phenylenediamine, 2,4-bis(trifluoromethyl)difluoro-1,3-phenylenediamine, 4,5-bis(trifluoromethyl)difluoro-1,3-phenylenediamine, 2,3-bis(trifluoromethyl)difluoro-1,4-phenylenediamine, 2,5-bis(trifluoromethyl)difluoro-1,4-phenylenediamine, 3,4-bis(trifluoromethyl)difluoro-1,2-phenylenediamine, 3-trifluoromethoxytrifluoro-1,2-phenylenediamine, 4-trifluoromethoxytrifluoro-1,2-phenylenediamine, 2-trifluoromethoxytrifluoro-1,3-phenylenediamine, 4-trifluoromethoxytrifluoro-1,3-phenylenediamine, 5,-trifluoromethoxytrifluoro-1,3-phenylenediamine, 2-trifluoromethoxytrifluoro-1,4-phenylenediamine, 3,4,5-tris(trifluoromethyl)fluoro-1,2-phenylenediamine, 3,4,6-tris(trifluoromethyl)fluoro-1,2-phenylenediamine, 2,4,5-tris(trifluoromethyl)fluoro-1,3-phenylenediamine, 2,4,6-tris(trifluoromethyl)fluoro-1,3-phenylenediamine, 4,5,6-tris(trifluoromethyl)fluoro-1,3-phenylenediamine, tetrakis(trifluoromethyl)-1,2-phenylenediamine, tetiakis(trifluoromethyl)-1,3-phenyleneimine, tetrakis(trifluoromethyl)-1,4-phenylenediamine, 3,3'-diaminooctafluorobiphenyl, 3,4'-diaminooctafluorobiphenyl, 4,4'-diaminooctafluorobiphenyl, 3,3'-diaminooctachlorobiphenyl, 3,4'-diaminooctachlorobiphenyl 4,4'-diaminooctachlorobiphenyl, 2,2'-bis(trichloromethyl)4,4'-diaminohexachlorobiphenyl 3,3'-bis(trichloromethyl)-4,4'-diaminohexafluorobiphenyl, bis(4-aminotetrafluorophenyl) dichloromethane, 1,2-bis(4-aminotetrafluorophenyl) tetrachloroethane, 2,2-bis(4-aminotetrafluorophenyl) hexachloropropane, 2,2'-bis(trifluoromethyl)-4,4'-diaminohexachlorobiphenyl, 3,3'-bis(trifiuoromethyl)-4,4'-diaminohexafluorobiphenyl, bis(4-aminotetrafluorophenyl) difluoromethane, 1,2-bis(4-aminotetrafluorophenyl) tetrachloroethane, 2,2-bis(4-aminotetrafluorophenyl) hexafluoropropane, bis(3-anminotetrafluorophenyl)ether, 3,4'-diaminooctafluorobiphenylether, bis(4-aminotetrafluorophenyl)ether, bis(3-aminotetrachlorophenyl)ether, 3,4'-diaminooctachlorobiphenylether, bis(4-aminotetrachlorophenyl)ether, 3,3'-diaminooctafluorobenzophenone, 3,4'-diaminooctafluorobenzophenone, 4,4'-diaminooctafluorobenzophenone, bis(3-aminotetrafluorophenyl)sulfone, 3,4'-diaminooctafluorobiphenylsulfone, bis(4-aminotetrafluorophenylsulfone), bis(3-aminotetrafluorophenyl)sulfide, 3,4'-diaminooctafluorobiphenylsulfide, bis(4-aniinotetrafluorophenyl)sulfide, 4-aminotetrafluorophenoxy-4'-aminotetrafluorophenyldifluoromethane, bis(4-aminotetrafluorophenoxy)difluoromethane, 1,2-bis(4-aminotetrafluorophenoxy)tetrafluoroethane, 2,2-bis(4-aminotetrafluorophenoxy)hexafluoropropane, bis(4-aminotetrafluorophenoxy)dichloromethane, 1,2-bis(4-aminotetrafluorophenoxy)tetrachloroethane, 2,2-bis(4-aminotetraflurophenoxy)hexachloropropane, 4,4"-diaminododecafluoro-p-terphenyl, 2',3'-bis(trifluoromethyl)-4,4"-diamino-p-terphenyl, 2,2"-bis(trifluoromethyl)-4,4"-diamino-p-terphenyl, 2',5'-bis(trifluoromethyl)-4,4"-diaminoterphenyl 2,7-diaminohexafluorodibenzofuran, 1,4-bis(4-aminotetrafluorophenoxy)tetrafluorobenzene, 2,6-diaminohexafluoronaphthalene, 2,7-diaminooctafluorophenanthrene, 2,6-diaminooctafluoroanthracene, 2,7-diaminohexathianthrene, 2,6-diaminohexafluoroanthraquinone, 2,6-diaminohexafluorobiphenylene, 2,6-diaminooxtafluoroanthrone, 2,7-diaminotetrafluorodibenz[b,e]1,4-dioxane, 2,2'-bis(4-aminophenyl) hexafluoropropane, 2,2'-bis(4-aminophenyl) hexachloropropane, 2,4-diaminobenzotrifluoride, 2,2-bis(trifluoromethyl)benzidine, 2,2-bis[4-(4-amino-2-trifluorophenoxy)phenyl]hexafluoropropane, 2,2-bis[4-(4-amino-2-trifuorophenoxy)phenyl]hexachloropropane, 3,4-diaminobenzotrifluoride, 3,5-diaminobenzotrifluoride, 2,5-diaminobenzotrifluoride, 2,2-bis[4-(4-aminophenoxy) phenyl]hexafluoropropane, 2,2-bis[4-(4-aminophenoxy) phenyl]hexachloropropane, or 3,4-diamino-1-fluorobenzene.

Hereinafter, the present invention will be described in detail through the following examples.

However, the present invention is not limited to the following examples. The following monomer synthesis examples iustrate preparations of bis(trisubstitutedtrimelitic)anhydride derivatives corresponding to formula (1).

<Monomer Synthesis Example 1>

0.015 mol of 3,5,6-trichloro-4-chloroformylphthalic anhydride (TCPA) was added to 10 ml of acetonitrile, and the mixture was then cooled down to –18° C. 0.0075 mol of hydroquinone, 0.015 mol of pyridine and 7 ml of acetonitrile were added to the reaction mixture under nitrogen atmosphere while the temperature was kept at –18° C.

The reaction mixture was stirred at –18° C. for 1 hour and at room temperature for another 1 hour. After the reaction is completed, the resulting precipitate was filtered and then washed with chloroform several times. The resulting product was dried in an oven set at 60° C. for 24 hours to yield 3,5,6-trichloro-4-chloroformylphthalic anhydride hydroquinone (yield: 92%).

<Monomer Synthesis Example 2>

3,5,6-Trichloro-4-chloroformylphthalic anhydride tetrafluorohydroquinone was obtained by the same method as in Synthesis Example 1, except that 0.0075 mol of tetrafluorohydroquinine was used instead of 0.0075 mol of hydroquinone (yield: 85%).

<Monomer Synthesis Example 3>

3,5,6-Trichloro-4-chloroformylphthalic anhydride tetrachlorohydroquinone was obtained by the same method as in Synthesis Example 1, except that 0.0075 mol of tetrachlorohydroquinine was used instead of 0.0075 mol of hydroquinone (yield: 88%).

<Monomer Synthesis Example 4>

3,5,6-Trichloro-4-chloroformylphthalic anhydride 4,4'-hydroxydiphenyl-2,2-propane was obtained by the same method as in Synthesis Example 1, except that 0.0075 mol of 4,4'-hydroxydiphenyl-2,2-propane was used instead of 0.0075 mol of hydroquinone (yield: 84%).

<Monomer Synthesis Example 5>

3,5,6-Trichloro-4-chloroformylphthalic anhydride 2,2-bis(4-hydroxyphenyl)hexafluoropropane was obtained by the same method as in Synthesis Example 1, except that 0.0075 mol of 2,2-bis(4-hydroxyphenyl)hexafluoropropane was used instead of 0.0075 mol of hydroquinone (yield: 78%).

<Monomer Synthesis Example 6>

3,5,6-Trichloro-4-chloroformylphthalic anhydride 2,2-bis(4-hydroxyphenyl) hexachloropropane was obtained by the same method as in Synthesis Example 1, except that 0.0075 mol of 2,2-bis(4-hydroxypheny)hexachloropropane was used instead of 0.0075 mol of hydroquinone (yield: 75%).

<Monomer Synthesis Example 7>

3,5,6-Trichloro-4-chloroformylphthalic anhydride 4,4-dihydroxy-3,3'-dichlorodiphenyl-2,2-propane was obtained by the same method as in Synthesis Example 1, except that 0.0075 mol of 4,4-dihydroxy-3,3'-dichlorodiphenyl-2,2-propane was used instead of 0.0075 mol of hydroquinone (yield: 83%).

<Monomer Synthesis Example 8>

3,5,6-Trichloro-4-chloroformylphthalic anhydride 2,2-bis(4-hydroxy-2,3,5-trichlorophenyl)propane was obtained by the same method as in Synthesis Example 1, except that 0.0075 mol of 2,2-bis(4-hydroxy-2,3,5-trichlorophenyl)propane was used instead of 0.0075 mol of hydroquinone (yield: 84%).

<Monomer Synthesis Example 9>

3,5,6-Trichloro-4-chloroformyiphthalic anhydride 4,4'-dihydroxy-3,3',5,5'-tetrachlorodiphenyl-2,2-propane was obtained by the same method as in Synthesis Example 1, except that 0.0075 mol of 4,4'-dihydroxy-3,3',5,5'-tetrachlorodiphenyl-2,2-propane was used instead of 0.0075 mol of hydroquinone (yield: 86%).

<Monomer Synthesis Example 10>

3,5,6-Trichloro-4chloroformylphthaiic anhydride 4,4'-dihydroxydiphenylether was obtained by the same method as in Synthesis Example 1, except that 0.0075 mol of 4,4'-dihydroxydiphenylether was used instead of 0.0075 mol of hydroquinone (yield: 81%)

<Monomer Synthesis Example 11>

3,5,6-Trichloro-4-chloroformylphthalic anhydride 4,4'-dihydroxy-3,3'-dichlorodiphenylsulfone was obtained by the same method as in Synthesis Example 1, except that 0.0075 mol of 4,4'-dihydroxy-3,3'-dichlorodiphenylsulfone was used instead of 0.0075 mol of hydroquinone (yield: 75%).

<Monomer Synthesis Example 12>

3,5,6-Trichloro-4-chloroformylphthalic anhydride 3,3'-difluoro-(1,1'-biphenyl)-4,4'-diol was obtained by the same method as in Synthesis Example 1, except that 0.0075 mol of 3,3'-difluoro-(1,1'-biphenyl)-4,4'-diol was used instead of 0.0075 mol of hydroquinone (yield: 77%).

The following polymer example illustrate preparations of polymers corresponding to formula (2).

<Polymer Example 1>

A mixture of 0.001 mol of paraphenylenebis(3,5,6-trichlorotrimellitic anhydride), 0.001 mol of 1,3-phenylenedianiine and 3 ml of N,N-dimethylacetamide was reacted at room temperature for 9 days under nitrogen atmosphere.

The reaction mire was precipitated using distilled water, and the resulting precipitate was filtered and then washed with distilled water several times. The resulting product was dried in an oven set at 60° C. for 24 hours in a vacuum, and then heated at 250° C. to yield polyesteiimide (PEI) (1) (yield: 90%).

<Polymer Example 2>

A mixture of 0.001 mol of paraphenylenebis(3,5,6-trichlorotrinellitic anhydride), 0.001 mol of 4,4'-diaminobiphenyl and 4ml of N,N-dimethylacetamide was reacted at room temperature for 9 days under nitrogen atmosphere.

The reaction mixture was precipitated using distilled water, and the resulting precipitate was filtered and then washed with distilled water several times. The resulting product was dried in an oven set at 60° C. for 24 hours in a vacuum, and then heated at 250° C. to yield PEI (2) (yield: 87%).

<Polymer Example 3>

A mixture of 0.001 mol of 2,3,5,6-tetrafluorophenylene-1,4-bis(3,5,6-trichloromellitic anhydride), 0.001 mol of tetrafluoro-1,3-phenylenediamine and 5 ml of N,N-dimethylacetamide was reacted at room temperature for 9 days under nitrogen atmosphere.

The reaction miture was precipitated using distilled water, and the resulting precipitate was filtered and then washed with distilled water several times. The resulting product was dried in an oven set at 60° C. for 24 hours in a vacuum, an acetic anhydride and pyridine were added to the dried mixture and then heated.

The reaction product was precipitated again into distilled water, and the precipitate was filtered and then washed with distilled water several times. The resulting product was dried in an oven set at 60° C. for 24 hours in a vacuum to yield PEI (3) (yield: 81%).

<Polymer Example 4>

A mixture of 0.001 mol of 2,3,5,6-tetrafluorophenylene-1,4-bis(3,5,6-trichloromellitic anhydride), 0.001 mol of 4,4'-diaminooctafluorophenyl and 3 ml of N,N-dimethylacetamide was reacted at room temperature for 9 days under nitrogen atmosphere.

The reaction mixture was precipitated using distilled water, and the resulting precipitate was filtered and then washed with distilled water several times. The resulting product was dried in an oven set at 60° C. for 24 hours in a vacuum, an acetic anhydride and pyridine were added to the dried mixture and then heated.

The reaction product was precipitated again into distilled water, and the precipitate was filtered and then washed with distilled water several times. The resulting product was dried in an oven set at 60° C. for 24 hours in a vacuum to yield PEI (4) (yield: 85%).

<Polymer Example 5>

A mixture of 0.001 mol of 2,2-isopropylidenediphenylbis (3,5,6-trichlorotrimellitic anhydride), 0.001 mol of 2,2'-bis(4-aminophenyl)hexachloropropane and 4 ml of N,N-dimiethylacetamide was reacted at room temperature for 9 days under nitrogen atmosphere.

The reaction mixture was precipitated using distilled water, and the resulting precipitate was fltered and then washed with distilled water several times. The resulting product was dried in an oven set at 60° C. for 24 hours in a vacuum, and then heated at 250° C. to yield PEI (5) (yield: 86%).

<Polymer Example 6>

A mixture of 0.001 mol of 2,2-isopropylidenediphenylbis (3,5,6-trichlorotrimellitic anhydride), 0.001 mol of 2,2'-bis (4-aminophenyl)propane and 3 ml of N,N-dimethylacetamide was reacted at room temperature for 9 days under nitrogen atmosphere.

The reaction mixture was precipitated using distilled water, and the resulting precipitate was filtered and then washed with distilled water several times. The resulting product was dried in an oven set at 60° C. for 24 hours in a vacuum, and then heated at 250° C. to yield PEI (6) (yield: 82%).

<Polymer Example 7>

A mixture of 0.001 mol of 1,3-hexachloroisopropylidene2,2-diphenylbis(3,5,6-trichlorotrimellitic anhydride), 0.001 mol of 2,2'-bis(4-aminotetafluorophenyl)hexafluoropropan and 3 ml of N,N-dimethylacetamide was reacted at room temperature for 9 days under nitrogen atmosphere.

The reaction mixture was precipitated using distilled water, and the resulting precipitate was filtered and then washed with distilled water several times. The resulting product was dried in an oven set at 60° C. for 24 hours in a vacuum, and then heated at 250° C. to yield PEI (7) (yield: 78%).

<Polymer Example 8>

A mixture of 0.001 mol of 1,3-hexachloroisopropylidene-2,2-diphenylbis(3,5,6-trichlorotrieitic anhydride), 0.001 mol of 2,2'-bis(4-aminotetrafluorophenyl)hexachloropropane and 5 ml of N,N-dimethylacetamide was reacted at room temperature for 9 days under nitrogen atmosphere.

The reaction mixue was precipitated using distilled water, and the resulting precipitate was filtered and then washed with distilled water several times. The resulting product was dried in an oven set at 60° C. for 24 hours in a vacuum, and then heated at 250° C. to yield PEI (8) (yield: 80%).

<Polymer Example 9>

A mixture of 0.001 mol of 2,2'-isopropylidene-3,3'-dichlorodiphenylbis(3,5,6-trichlorotrimellitic anhydride), 0.001 mol of bis(4-aminophenyl)ether and 5 ml of N,N-dimethylacetamide was reacted at room temperature for 9 days under nitrogen atmosphere.

The reaction mixture was precipitated using distilled water, and the resulting precipitate was filtered and then washed with distilled water several times. The resulting product was dried in an oven set at 60° C. for 24 hours in a vacuum, and then heated at 250° C. to yield PEI (9) (yield: 79%).

<Polymer Example 10>

A mixture of 0.001 mol of 2,2'-isopropylidene-3,3'-dichlorodiphenylbis(3,5,6-trichlorotrimellitic anhydride), 0.001 mol of 2,2-bis(trifluoromethyl)benzidine and 5 ml of N,N-dimethylacetamide was reacted at room temperature for 9 days under nitrogen atmosphere.

The reaction mixture was precipitated using distilled water, and the resulting precipitate was filtered and then washed with distilled water several times. The resulting product was dried in an oven set at 60° C. for 24 hours in a vacuum and then heated at 250° C. to yield PEI (10) (yield: 75%).

<Polymer Example 11>

A mixture of 0.001 mol of 2,2'-isopropylidene-3,3',5,5'-tetrachlorodiphenylbis(3,5,6-trichlorotrimellitic anhydride), 0.001 mol of bis(4-aminotetrafluorophenyl)sulfone and 5 ml of N,N-dimethylacetamide was reacted at room temperature for 9 days under nitrogen atmosphere.

The reaction mixture was precipitated using distilled water, and the resulting precipitate was filtered and then washed with distilled water several times. The resulting product was dried in an oven set at 60° C. for 24 hours in a vacuum and then heated at 250° C. to yield PEI (11) (yield: 73%).

<Polymer Example 12>

A mixture of 0.001 mol of diphenyleneetherbis(3,5,6-trichlorotrimellitic anhydride), 0.001 mol of bis(4-aminotetrachlorophenyl)ether and 5 ml of N,N-dimethylacetamide was reacted at room temperature for 9 days under nitrogen atmosphere.

The reaction mixture was precipitated using distilled water, and the resulting precipitate was filtered and then washed with distilled water several times. The resulting product was dried in an oven set at 60° C. for 24 hours in a vacuum and then heated at 250° C. to yield PEI (12) (yield: 68%).

Also, thermal stability, opticalloss at a near infrared wavelength of 1,000~1,700 nm, and film processing property of the PEI (1) through PEI (12) synthesized by Examples 1 through 12 were measured. Here, the thermal stability of the polyesterimide was measured using a thermogravimetry analysis (TGA) method.

As a result, it was ascertained that the thermal stability was good in all the PEI (1) through PEI (15) from the fact that the thermal decomposition occurred in the range of approximately 350~450° C.

Also, it can be understood that the optical loss of the polyesterimide is simlar to or less than the conventional perfluorinated polyimide.

Also, a conventional partially fluorinated or perfluorinated polyesterimide is difficult to be applied practically due to its poor film processing property. The polyesterimides obtained by Examples 1 through 12 have an improved film processing property compared to the conventional polyimide.

The polyesterimide according to the present invention has a higher refractive index than the conventional fluorinated polyimide. Thus, when using such polyesterimide as a material for the core of an optical fiber, the range of the meterials that can be selected for the cladding becomes wide. Also, the coating property and adhesion to a substrate are improved compared to the conventional polyimide, thereby providing a good film forming property and thermal stability.

Also, because the polyesterimide according to the present invention can minimize optical loss at a near infrared wavelength range, the polyesterimide of the present invention is very useful as an optical material in the optical communications field adopting the light of near infrared wavelength That is, the polyesterrimide according to the present invention can be used as a functional polymeric material having a low optical loss characteristic which is essential for manufacturing an optical device for optical waveguiding, such as optoelectronic integrated circuit (OEIC), opto-electrical mixed wiring board (OEMWB), hybrid integration device, multi-chip module (MCM) or plastic optical fiber.

What is claimed is:

1. A composition of matter, comprising a bis(trisubstitutedtrimellitic anhydride) derivative represented by the chemical formula:

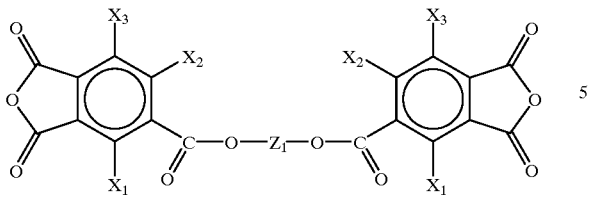

wherein $X_1$, $X_2$, and $X_3$ are independently selected from the group consisting of halogen atom, halogenated alkyl group, halogenated aromatic ring group, —$NO_2$, —$OR^1$ and $SR^1$ (where $R^1$ is halogenated alkyl or halogenated aromatic ring group);

and where $Z_1$ is selected from the group consisting of divalent halogenated aliphatic hydrocarbon, divalent halogenated aliphatic cyclic hydrocarbon and divalent halogenated aromatic hydrocarbon.

2. The composition of matter of claim 1, wherein $X_1$, $X_2$, and $X_3$ are independently selected from the group consisting of chloride atom, partially or perchlorinated alkyl groups, partially or perchlorinated aromatic ring groups, partially or perchlorinated alkoxy groups, and partially or perchlorinated phenoxy groups.

3. The composition of matter of claim 1, wherein $Z_1$ is selected from the group consisting of divalent halogenated aliphatic hydrocarbon of $C_1$–$C_{25}$, divalent halogenated aliphatic cyclic hydrocarbon of $C_1$–$C_{25}$ and divalent halogenated aromatic hydrocarbon of $C_6$–$C_{25}$.

4. The composition of matter of claim 1, where $Z_1$ is selected from the group represented by the structural formula:

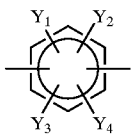

wherein $Y_1$, $Y_2$, $Y_3$ and $Y_4$ are independently selected from the group consisting of halogen atom, halogenated alkyl group, halogenated aromatic ring group, $NO_2$, —$OR^1$ and —$SR^1$ (where $R^1$ is a halogenated alkyl or halogenated aromatic ring group).

5. The composition of matter of claim 1, wherein $Z_1$ is selected from the group represented by the structural formula:

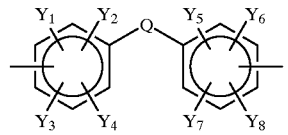

wherein $Y_1$, $Y_2$, $Y_3$, $Y_4$, $Y_5$, $Y_6$, $Y_7$ and $Y_8$ are independently selected from the group consisting of halogen atom, halogenated alkyl group, halogenated aromatic ring group, $NO_2$, —$OR^1$ and —$SR^1$ (where $R^1$ is halogenated alkyl or halogenated aromatic ring group); and Q represents either a single bond or is a radical selected from the group consisting of —O—, —CO—, —$SO_2$—, —S—, —(OT)$_m$—, —(OT)$_m$— and —(TO)$_m$—, where T is halogenated alkylene or halogenated arylene group and m is an integer from 1 to 10.

6. A polymer for optical communications, comprising a repeating unit represented by the chemical formula:

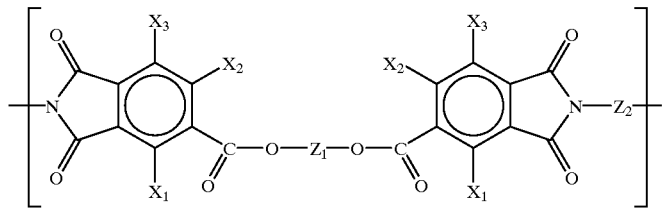

wherein $X_1$, $X_2$, and $X_3$ are independently selected from the group consisting halogen atom, halogenated alkyl group, halogenated aromatic ring group, —$NO_2$, —$OR^1$ and $SR^1$ (where $R^1$ is halogenated alkyl or halogenated aromatic ring group);

and where $Z_1$ and $Z_2$ are independently selected from the group consisting of divalent halogenated aliphatic hydrocarbon, divalent halogenated aliphatic cyclic hydrocarbon and divalent halogenated aromatic hydrocarbon.

7. The polymer of claim 6, wherein $X_1$, $X_2$, and $X_3$ are independently selected from the group consisting of chloride atom, partially or perchlorinated alkyl groups, partially or perchlorinated aromatic ring groups, partially or perchlorinated alkoxy groups, and partially or perchlorinated phenoxy groups.

8. The polymer of claim 6, wherein $Z_1$ and $Z_2$ are independently selected from the group consisting of divalent halogenated aliphatic hydrocarbon of $C_1$–$C_{25}$, divalent halogenated aliphatic cyclic hydrocarbon of $C_1$–$C_{25}$ and divalent halogenated aromatic hydrocarbon of $C_1$–$C_{25}$.

9. The polymer of claim 6, wherein $Z_1$ and $Z_2$ are independently selected from the group represented by the following structural formula:

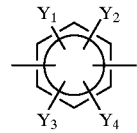

wherein $Y_1$, $Y_2$, $Y_3$ and $Y_4$ are independently selected from the group consisting of halogen atom, halogenated alkyl group, halogenated aromatic ring group, —NO$_2$, —OR$^1$ and SR$^1$ (where R$^1$ is halogenated alkyl or halogenated aromatic ring group).

10. The polymer of claim 6, wherein Z$_1$ and Z$_2$ are independently selected from the group represented by the following structural formula:

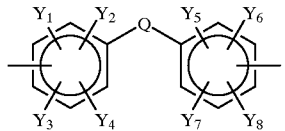

wherein Y$_1$, Y$_2$, Y$_3$, Y$_4$, Y$_5$, Y$_6$, Y$_7$ and Y$_8$ are independently selected from the group consisting of halogen atom, halogenated alkyl group, halogenated aromatic ring group, —NO$_2$, —OR$^1$ and SR$^1$ (where R$^1$ is halogenated alkyl or halogenated aromatic ring group); and Q is a simple chemical bond or selected from the group consisig of , —O—, —CO—, —SO$_2$—, —S—, —(OT)$_m$—, —(TO)$_m$— and —(OTO)$_m$—, where T is a halogenated alkylene or halogenated arylene group and m is an integer from 1 to 10.

11. The polymer of claim 6, wherein the polymer has a molecular weight in the range of approximately 1×10$^4$ to 5×10$^5$ Dalton.

12. The polymer of claim 6, wherein the polymer has a thermal decomposition temperature in the range of approximately 300 to 500° C.

13. The polymer of claim 6, wherein the polymer has a glass transition temperature in the range of approximately 190–290° C.

14. The composition of matter of claim 1, where said bis(trisubstitutedtrimellitic anhydride) derivative is selected from the group consisting of 3,5,6-trichloro-4-chloroformylphthalic anhydride hydroquinone, 3,5,6-trichloro-4-chloroformylphthalic anhydride tetrafluorohydroquinone, 3,5,6-trichloro-4-chloroformylphthalic anhydride tetrachlorohydroquinone, 3,5,6-trichloro-4-chloroformylphthalic anhydride 4,4'-hydroxydiphenyl-2,2-propane, 3,5,6-trichloro-4-chloroformylphthalic anhydride 2,2-bis(4-hydroxyphenyl)hexafluoropropane, 3,5,6-trichloro-4-chloroformylphthalic anhydride 2,2-bis(4-hydroxyphenyl)hexachloropropane, 3,5,6-trichloro-4-chloroformylphthalic anhydride 4,4-dihydroxy-3,3'-dichlorodiphenyl-2,2-propane, 3,5,6-trichloro-4-chloroformylphthalic anhydride 2,2-bis(4-hydroxy-2,3,5-trichlorophenyl)propane, 3,5,6-tichloro-4-chloroformylphthalic anhydride 4,4'-dihydroxy-3,3',5,5'-tetrachlorodiphenyl-2,2-propane, 3,5,6-trichloro-4-chloroformylphthalic anhydride 4,4'-dihydroxydiphenylether, 3,5,6-trichloro-4-chloroformylphthalic anhydride 4,4'-dihydroxy-3,3'-dichlorodiphenylsulfone, and 3,5,6-trichloro-4-chloroformylphthalic anhydride 3,3'-difluoro-(1,1'-biphenyl)-4,4'-diol.

15. A polymer prepared by the reaction of a diamine compound with a compound selected from the group consistng of 3,5,6-trichloro-4-chloroformylphthalic anhydride hydroquinone, 3,5,6-trichloro-4-chloroformylphthalic anhydride tetrafluorohydroquinone, 3,5,6-trichloro-4-chloroformylphthalic anhydride tetrachlorohydroquinone, 3,5,6-trichloro-4-chloroformylphthalic anhydride 4,4'-hydroxydiphenyl-2,2-propane, 3,5,6-trichloro-4-chloroformylphthalic anhydride 2,2-bis(4-hydroxyphenyl)hexafluoropropane, 3,5,6-trichloro-4-chloroformylphthalic anhydride 2,2-bis(4-hydroxyphenyl)hexachloropropane, 3,5,6-trichloro-4-chloroformylphthalic anhydride 4,4-dihydroxy-3,3'-dichlorodiphenyl-2,2-propane, 3,5,6-trichloro-4-chloroformylphthalic anhydride 2,2-bis(4-hydroxy-2,3,5-trichlorophenyl)propane, 3,5,6-trichloro-4-chloroformylphthaic anhydride 4,4'-dihydroxy-3,3',5,5'-tetrachlorodiphenyl-2,2-propane, 3,5,6-trichloro-4-chloroformylphthalic anhydride 4,4'-dihydroxydiphenylether, 3,5,6-trichloro-4-chloroformylphthalic anhydride 4,4'-dihydroxy-3,3'-dichlorodiphenylsulfone, and 3,5,6-trichloro-4-chloroformylphthalic anhydride 3,3'-difluoro-(1,1'-biphenyl)-4,4'-diol.

16. A polymer prepared by the reaction of a diamine compound with a compound selected from the group consisting of paraphenylenebis(3,5,6-trichlorotrimellitic anhydride), 2,3,5,6-tetrafluorophenylene-1,4-bis(3,5,6-trichloromellitic anhydride), 2,2-isopropylidenediphenylbis(3,5,6-trichlorotrimellitic anhydride), 1,3-hexachloroisopropylidene-2,2-diphenylbis(3,5,6-trichlorotrimellitic anhydride), 2,2'-isopropylidene-3,3'-dichlorodiphenylbis(3,5,6-trichlorotrimellitic anhydride), and diphenyleneetherbis(3,5,6-trichlorotrimellitic anhydride).

* * * * *